United States Patent [19]

Kolozsi

[11] Patent Number: 5,108,381
[45] Date of Patent: Apr. 28, 1992

[54] TISSUE SAMPLE COLLECTION TRAP

[76] Inventor: William Z. Kolozsi, 2380 Southeast Blvd., Salem, Ohio 44460

[21] Appl. No.: 667,225

[22] Filed: Mar. 11, 1991

[51] Int. Cl.$^5$ .............. A61M 1/00; B01D 35/00; B01D 45/00; A61B 10/00
[52] U.S. Cl. .................. 604/319; 604/317; 604/322; 604/324; 604/326; 128/749; 128/760; 210/416.1; 210/406; 210/436; 55/478; 55/270
[58] Field of Search ............. 604/317, 319, 322, 324, 604/326; 128/749, 750, 752, 753, 758, 760; 55/478; 210/406, 416.1, 436

[56] References Cited

U.S. PATENT DOCUMENTS

| | | | |
|---|---|---|---|
| 37,500 | 1/1863 | Fontain | 55/478 |
| 2,784,717 | 3/1957 | Thompson | 128/276 |
| 3,929,133 | 12/1975 | Ragab | 128/277 |
| 3,982,538 | 9/1976 | Sharpe | 128/276 |
| 4,190,020 | 2/1980 | Tamas et al. | 119/14.08 |
| 4,384,580 | 5/1983 | Leviton | 604/119 |
| 4,385,590 | 5/1983 | Mortensen | 119/14.01 |
| 4,430,084 | 2/1984 | Deaton | 604/317 |
| 4,643,197 | 2/1987 | Greene et al. | 128/762 |

Primary Examiner—Randy C. Shay
Assistant Examiner—A. P. Zuttarelli
Attorney, Agent, or Firm—Frederic E. Naragon

[57] ABSTRACT

A tissue sample collection trap for trapping tissue samples for use with a suction sample collecting device comprising a cylindrical container either translucent or opaque with a suction connector element with a port provided at one end to connect to and cooperate with a suction device and the opposite container end open and adapted to accept a cap, the cap being either solid for continuous suction or provided with a control port through the end and into the container to be manually obstructed for suction by the operator and the diameter of a section of the inside of the container at the suction connector element and reduced forming a ledge adapted to hold a removable tissue trap assembly, and a tissue trap assembly comprising two round discs with a plurality of perforations forming screens and adapted to trap specimens and to slidably engage with and within the container and a hollow tubular handle provided to separate the discs extending axially and through the discs for slidably removing the tissue trap assembly from the container and providing a relief pathway for flow of excessive suction, and a collector connector means with a port provided on the perimeter of the container which is either permanent and molded to the container or is a coupling element adapted to accept various sizes and styles of connectors and is adapted to connect to and cooperate with a suction sample collecting device.

19 Claims, 3 Drawing Sheets

TISSUE SAMPLE COLLECTION TRAP

BACKGROUND OF THE INVENTION

This invention pertains to a Tissue Sample Collection Trap to be used primarily in conjunction with devices that collect tissue samples via a suction apparatus. The present invention is a device directed to the separation of tissue material from the suction effluent obtained from a patient, primarily via an endoscopic instrument, or via a tissue obtaining apparatus. The prior art disclosed patents for tissue sample collection. Some of the patents are listed below. U.S. Pat. No. 2,784,717—Thompson, March, 1957 U.S. Pat. No. 3,929,133—Ragab, December, 1975 U.S. Pat. No. 3,982,538—Sharpe, September, 1976 U.S. Pat. No. 4,190,020—Tamas Et. al., February, 1980 U.S. Pat. No. 4,384,580—Leviton, May, 1983 U.S. Pat. No. 4,385,590—Mortensen, May, 1983 U.S. Pat. No. 4,430,084—Deaton, February, 1984 U.S. Pat. No. 4,643,197—Greene et. al., February, 1987

U.S. Pat. No. 4,643,197 issued to Greene et. al. discloses a tissue trap assembly which contains a filter system with a plurality of traps within a filter assembly. The filter is movable relative to the inlet for effluent flow to select the trap which is to collect the tissue specimen. The invention does not allow for the removal of the filter system from the device for easy removal of the collected tissue samples. As such, when traps are used, the device must be removed from the suction line therefore disrupting procedure of tissue sample collection. The operator must then tediously remove the tissue samples from within the traps in the filter assembly. The invention also makes reference to a complicated external valve system to direct the flow of suction effluent through the trap or to a fluid collection system. No reference is made for the control of suction through the trap such as the controlling orifice making up a portion of the present invention.

U.S. Pat. No. 3,929,133 issued to Ragab discloses a complex filter assembly for the entrapment of product of conception removed by suction. The trap assembly is a complicated arrangement of thimble shaped sieves that separate the tissue. The configuration of the assembly and ports are such that the tissue specimens of the size intended for collection with the present invention would be lost. In addition, the device does not allow for changing the trap assembly during use for easy separation of tissue specimens.

The other referenced U.S. Patents provide for devices for the collection of effluent only and do not provide means for entrapment of tissue specimens. The cited patents teach of collection of the suction effluent, but do not provide any means for separation of tissue from the effluent. In addition, such patents teach of devices that are very large and intended to be placed in wall holders, or the floor for collection of large amounts of suction effluent.

The present invention provides a novel tissue separation system for the recovery of tissue samples from the suction effluent. The present invention can be hand held with control of the suction flow through the device without valves.

The present invention differs from the prior art and provides a novel tissue sample collection trap in that the device can be hand held and suction flow control is provided by an opening in the top of a removal cap rather than the use of complex and expensive valves. Further, a continuous flow of suction can be achieved by utilizing a removable cap with a solid top. The present invention allows for the entrapment of small tissue samples from the effluent by an easy to remove screen assembly that is made of an entrapment screen and a handle assembly that also serves as an overflow or excess suction relief port.

SUMMARY OF THE INVENTION

The present invention is a tissue collection trap that is used to collect tissue specimens primarily from devices that use suction for the retrieval of the tissue sample. This device overcomes the foregoing prior art and other drawbacks and provides a novel and improved tissue sample trap.

In accordance with the present invention a Tissue Sample Collection Trap is provided for trapping tissue samples primarily in collection systems utilizing suction. The device comprises a cylinder shaped container which can be opaque, or translucent to allow the operator to observe the tissue specimen being collected. At one end of the container a suction connector means is provided with a port into the container to connect and cooperate with a suction device and the container. The opposite end of the container is open and is adapted to accept a cap. A cap is provided that can either be solid for continuous suction or have a control port through the end of the cap into the container and cooperating therewith. The control port functions so that without obstruction of the control port, air is sucked into the container and passes through the control port of the cap and thereby decreases the flow of suction through the container. When suction is desired, the control port is obstructed manually by the operator's finger or thumb creating a vacuum. The diameter of a section of the inside of the container at the suction connector means end is reduced forming a ledge within that section of the container and is adapted to hold a tissue trap assembly. The tissue trap assembly comprises two round discs with perforations on the surface thereby forming screens and adapted to slidably engage with the container and a hollow tubular handle is provided to separate the discs and extends axially and through the discs for slidably placing and removing the tissue trap assembly from the container. The hollow handle also serves as a relief pathway for the flow of excessive suction and cooperates with the control port and connector suction means disposed at the cap and end of the container, respectively. The perforation size in the discs is provided such that solid tissue material being collected cannot pass through the discs but liquid effluent can. On the perimeter of the container a collector connector means is provided at a position between the open end of the container and the reduced diameter suction at the other end of the container to connect the container to any tissue sample collection device. The collector connector means is adapted to drain the collected sample from the collection device through a port in the collector connector means into the container. This connector means can be permanent and molded to the container or can consist of a coupling means so that the type of connector can be varied. Once tissue collection is complete, the cap can be removed and the trap assembly can be slidably removed from the open end of the container with the collected tissue sample. A new trap assembly can be slidably inserted for the collection of additional tissue specimens without the necessity of disconnecting the container from the tissue sample collecting device or suction means.

DETAILED DESCRIPTION OF THE DRAWINGS

Figure 1:
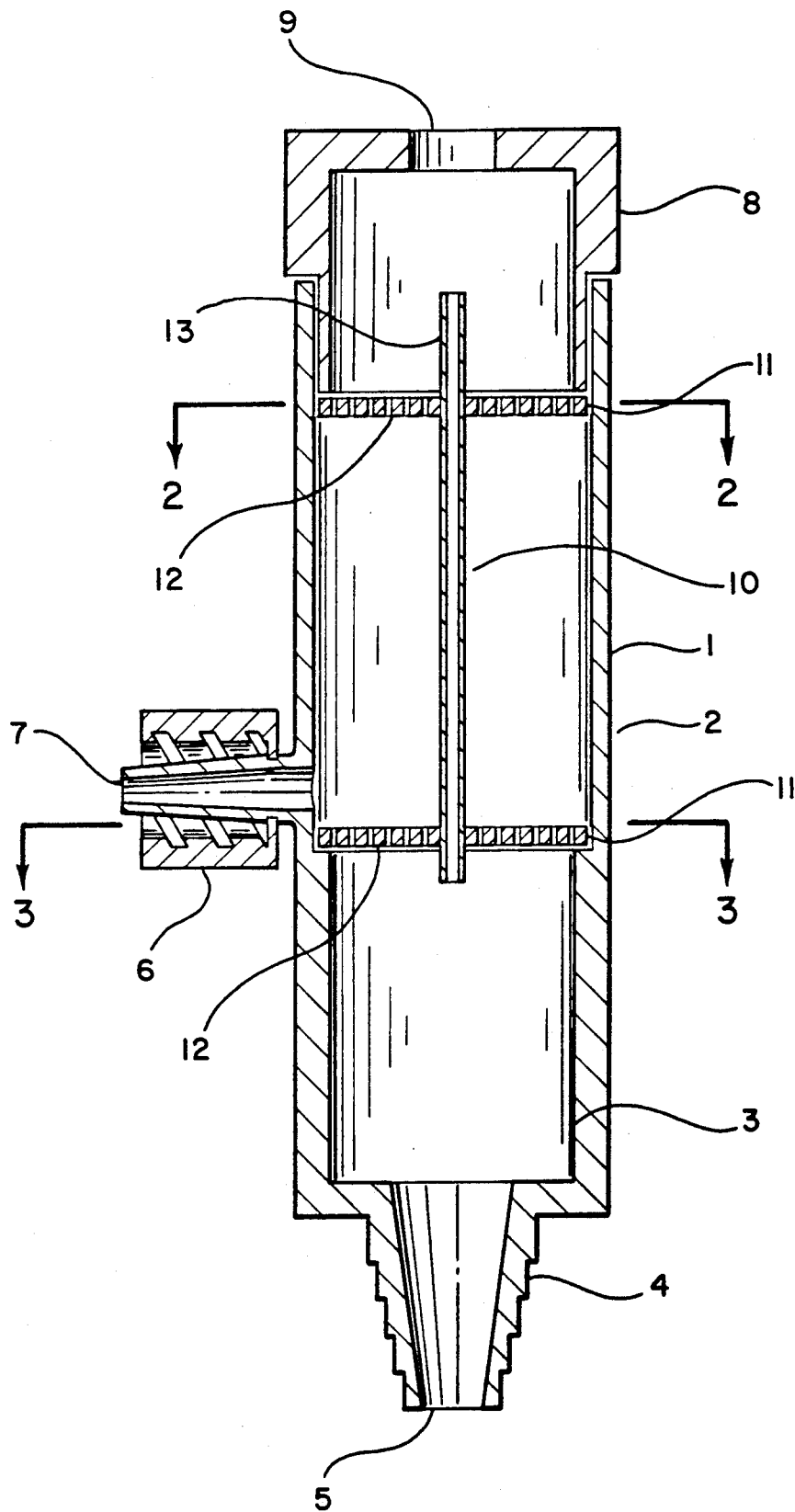
FIG. 1 is a sectioned perspective view of the preferred embodiment of the invention.

Reference is now made to the drawings wherein the present invention is illustrated in detail and wherein similar components bear the same reference numeral throughout the several views and drawings.

FIG. 1 illustrates a sectioned perspective view of the preferred embodiment of the invention, the entire invention generally referred to by numeral 1, is illustrated with a cylindrical container 2, with reduced diameter section 3, a suction connector means 4, with a port 5, a collector connecting coupling means 6, with port 7, a removable cap 8, with control port 9, a removable tissue trap assembly 10, with disc 11, disc with perforations 12, and hollow tubular handle 13.

Figure 2:
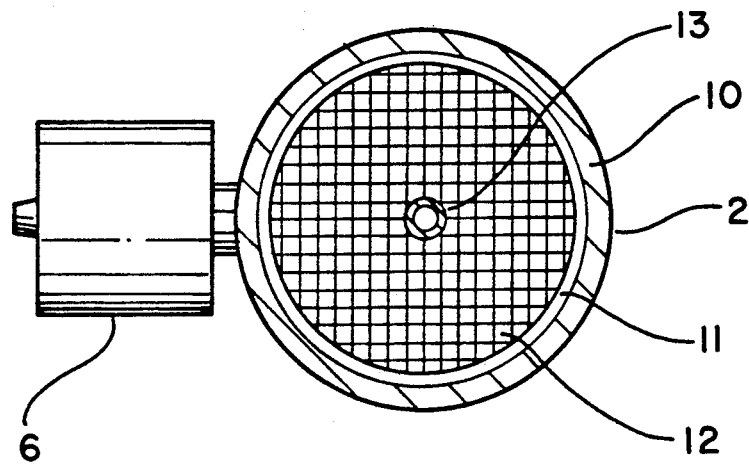
FIG. 2 is a cross-sectional view of FIG. 1 taken along line A—A.

FIG. 2 is a cross-sectional view of FIG. 1 taken along line A—A and illustrates a cylindrical container 2, with removable tissue trap assembly 10, with disc 11, perforations 12, and hollow tubular handle 13 and collector connecting coupling means 6.

Figure 3:
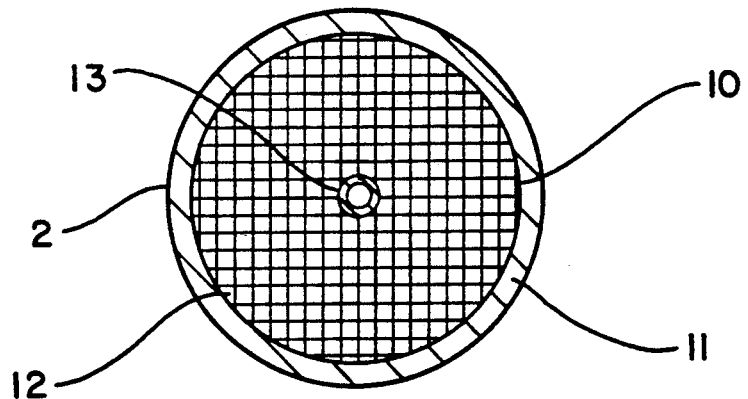
FIG. 3 is a cross-sectional view of FIG. 1 taken along line B—B.

FIG. 3 is a cross-sectional view of FIG. 1 taken along line B—B and illustrates a cylindrical container 2, with removable tissue trap assembly 10, with disc 11, and perforations 12, and hollow tubular handle 13.

Figures 4, 5:
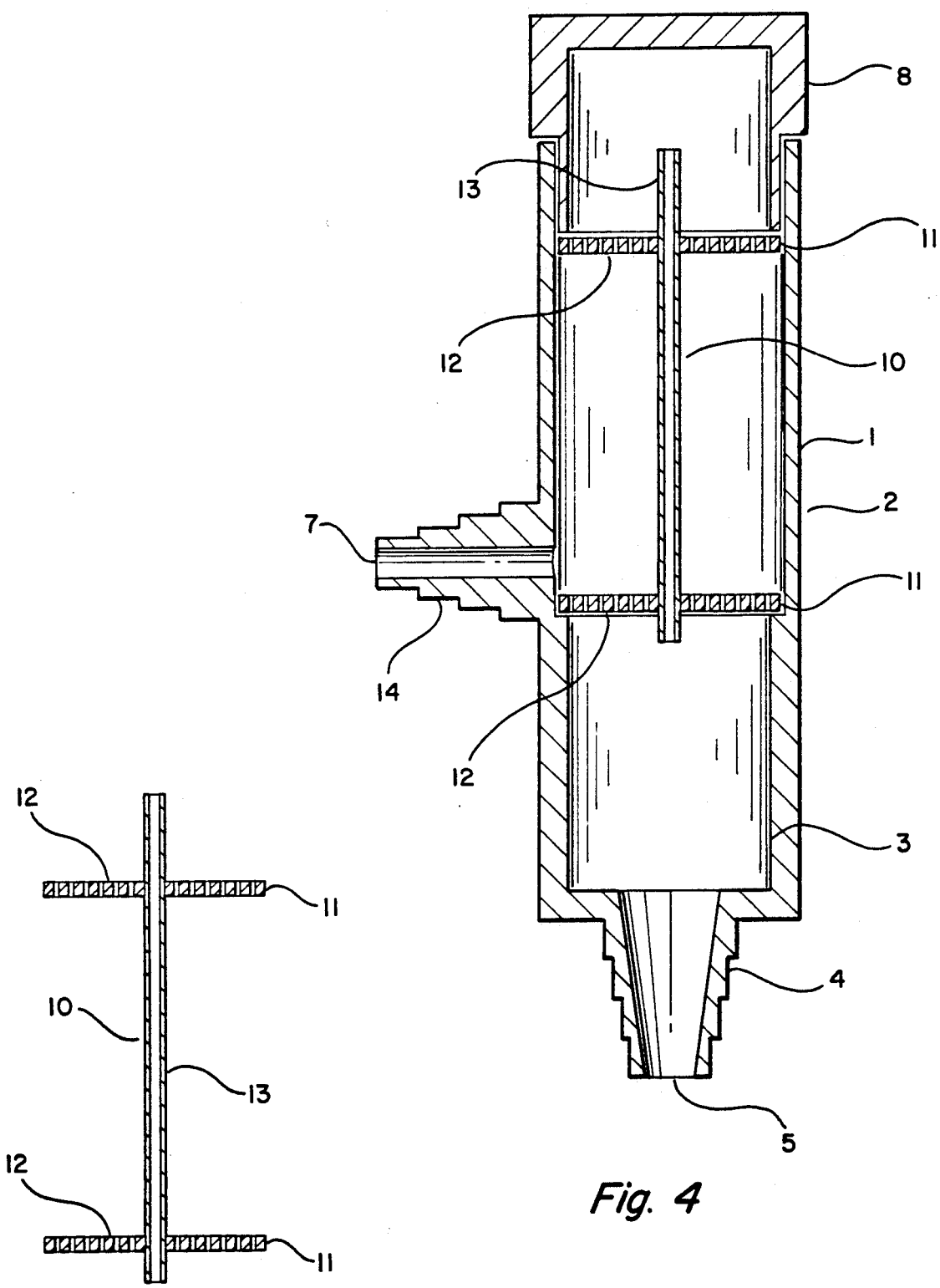
FIG. 4 is a sectioned perspective view of an alternative embodiment of the invention.
FIG. 5 is a sectional perspective view of the removable tissue trap assembly of the invention.

FIG. 4 illustrates a sectioned perspective view of an alternative embodiment of the invention, the entire invention referred to by numeral 1, is illustrated with cylindrical container 2, with reduced diameter section 3, a suction connector means 4, with port 5, a permanent molded collector connecting means 14, with port 7, a removable cap 8, a removable tissue trap assembly 10, with discs 11, with perforations 12, and hollow tubular handle 13.

FIG. 5 illustrates a sectioned perspective view of the removable tissue trap assembly 10, of the invention with discs 11, with perforations 12, and hollow tubular handle 13.

DESCRIPTION OF THE PREFERRED EMBODIMENT

Referring to FIGS. 1-5 the preferred embodiment of the present invention is a tissue sample collection trap generally referred to as numeral 1 comprising a translucent cylindric container 2, with reduced diameter section 3, a suction connector means 4, with port 5, collector connecting coupling means 6, with port 7, a removable cap 8, with control port 9, a removable tissue trap assembly 10, with discs 11, with perforations 12, and hollow tubular handle 13.

Although the invention has been described in preferred form with a certain degree of particularity, it is understood that the present disclosure of the preferred form has been made only by way of example and numerous changes in the details of construction and the combination arrangement of parts may be resorted to without departing from the spirit and the scope of the invention hereinafter claimed.

What is claimed is:

1. A tissue sample collection trap comprising a cylindrical container with a suction connector means provided at one end of the container with a port into the container and adapted to connect to a suction means and cooperating therewith, the opposite end of the container being open and adapted to accept a removable cap, a removable cap adapted to fit the container at the open end of the container, the diameter of a section of the inside of the container at the suction connector means end being reduced forming a ledge within that section of the container and adapted to hold a removable tissue trap assembly, a removable tissue trap assembly adapted to slidably engage with the container and comprising two round discs with a plurality of perforations on the surface thereby forming screens adapted to slidably engage with the container and to trap collected tissue samples while allowing effluent to flow through the screens and a hollow tubular handle provided to separate the discs and extend axially from the center of the discs and through the discs to provide a relief pathway for excessive suction and to provide for manual slidable removal of the tissue trap from the container, and a collector connector means with a port into the container extending radially on the perimeter of the container at a positon between the open end of the container and the reduced diameter section at the other end of the container and adapted to connect with a tissue sample collecting device and cooperating therewith to allow tissue samples to be drawn through a port in the collector connecting means and into the container from the tissue sample collecting device.

2. The tissue sample collection trap of claim 1 wherein the cap is solid to allow continuous suction within the container.

3. The tissue sample collection trap of claim 2 wherein the container is opaque.

4. The tissue sample collection trap of claim 3 wherein the collector connector means is permanent and is molded to the container.

5. The tissue sample collection trap of claim 3 wherein the collector connecting means comprises a coupling means adapted to accept various sizes and styles of connectors.

6. The tissue sample collection trap of claim 2 wherein the container is translucent to allow the operator to observe the tissue samples being collected.

7. The tissue sample collection trap of claim 6 wherein the collector connector means is permanent and is molded to the container.

8. The tissue sample collection trap of claim 6 wherein the collector connector means comprises a coupling means adapted to accept various sizes and styles of connectors.

9. The tissue sample collection trap of claim 2 wherein the collector connector means is permanent and is molded to the container.

10. The tissue sample collection trap of claim 2 wherein the collector connector means comprises a coupling means adapted to accept various sizes and styles of connectors.

11. The tissue sample collection trap of claim 1 wherein the cap has a control port formed through the end of the cap and into the container and cooperating therewith to allow air to flow through the container to the outside when the control port is not manually obstructed by the operator and to provide suction within the container when the control port is manually obstructed by the operator.

12. The tissue sample collection trap of claim 11 wherein the container is opaque.

13. The tissue sample collection trap of claim 11 wherein the container is translucent to allow the operator to observe the tissue samples being collected.

14. The tissue sample collection trap of claim 4 wherein the collector connector means is permanent and is molded to the container.

15. The tissue sample collection trap of claim 4 wherein the collector connector means comprises a coupling means adapted to accept various sizes and styles of connectors.

16. The tissue sample collection trap of claim 1 wherein the container is translucent to allow the operator to observe the tissue samples being collected.

17. The tissue sample collection trap of claim 1 wherein the collector connector means is permanent and is molded to the container.

18. The tissue sample collection trap of claim 1 wherein the collector connector means comprises a coupling means adapted to accept various sizes and styles of connectors.

19. The tissue sample collection trap of claim 1 wherein the container is opaque.

* * * * *